United States Patent
Whitely

(10) Patent No.: US 10,632,011 B2
(45) Date of Patent: Apr. 28, 2020

(54) THERMOTHERAPEUTIC PAD WITH BEADS IN TEXTURED ENVELOPE

(71) Applicant: Rapid Aid Corp., Mississauga (CA)

(72) Inventor: Jeffrey Thomas Whitely, Millgrove (CA)

(73) Assignee: RAPID AID CORP., Mississauga (CA)

( * ) Notice: Subject to any disclaimer, the term of this patent is extended or adjusted under 35 U.S.C. 154(b) by 868 days.

(21) Appl. No.: 14/136,639

(22) Filed: Dec. 20, 2013

(65) Prior Publication Data

US 2015/0173942 A1  Jun. 25, 2015

(51) Int. Cl.
*A61F 7/10* (2006.01)
*A61F 7/02* (2006.01)

(52) U.S. Cl.
CPC ........ *A61F 7/02* (2013.01); *A61F 2007/0209* (2013.01); *A61F 2007/0219* (2013.01); *A61F 2007/0228* (2013.01)

(58) Field of Classification Search
CPC ...... A61F 2007/0209; A61F 2007/0219; A61F 7/02
See application file for complete search history.

(56) References Cited

U.S. PATENT DOCUMENTS

| | | | |
|---|---|---|---|
| 3,780,537 A | 12/1973 | Spencer | |
| 4,756,311 A * | 7/1988 | Francis, Jr. | A61F 7/02 126/204 |
| 5,113,877 A * | 5/1992 | Johnson, Jr. | A61F 5/0111 128/869 |
| 5,417,720 A * | 5/1995 | Mason | A61F 5/05816 607/104 |
| 5,897,580 A * | 4/1999 | Silver | A61F 7/03 128/889 |
| 6,083,254 A | 7/2000 | Evans | |
| 6,524,331 B1 * | 2/2003 | Kohout | A61F 7/02 5/421 |
| 6,610,084 B1 | 8/2003 | Torres | |
| 6,916,334 B2 * | 7/2005 | Noonan | A61F 7/02 607/108 |
| 7,652,228 B2 | 1/2010 | Igaki et al. | |
| D660,445 S | 5/2012 | Baumwald | |

(Continued)

OTHER PUBLICATIONS

Hot/Cold Pack—Gel Pearl Technology—the Science of Soothing. Downloaded from http://web.archive.Org/web/20120801091911/http://www.therapearl.com/ . . . .

(Continued)

*Primary Examiner* — Kaitlyn E Smith
*Assistant Examiner* — Yasamin Ekrami
(74) *Attorney, Agent, or Firm* — Perry + Currier Inc.

(57) ABSTRACT

A thermotherapeutic pad includes a sealed envelope having a top layer of plastic and a bottom layer of textured plastic. The top layer of plastic and the bottom layer of textured plastic can be heat-sealed together. The bottom layer of textured plastic has an outer textured surface and is more thermally insulative than the top layer of plastic. A plurality of gel beads and liquid are contained inside the sealed envelope. The bottom layer of the pad can be placed against the skin or clothing to provide thermal therapy. Baffles can be provided inside the sealed envelope to promote even distribution of gel beads.

27 Claims, 6 Drawing Sheets

(56) References Cited

U.S. PATENT DOCUMENTS

| | | |
|---|---|---|
| D660,446 S | 5/2012 | Baltazar |
| D660,447 S | 5/2012 | Baltazar |
| D660,973 S | 5/2012 | Baumwald |
| D667,957 S | 9/2012 | Baumwald |
| D668,343 S | 10/2012 | Baumwald et al. |
| D668,344 S | 10/2012 | Baumwald et al. |
| D668,345 S | 10/2012 | Baumwald |
| D687,558 S | 8/2013 | Sonoda |
| D693,015 S | 11/2013 | Dubbe |
| D787,694 S | 5/2017 | Baltazar |
| 2004/0241366 A1* | 12/2004 | Ishida ............... A47G 9/10 428/36.1 |
| 2006/0235495 A1* | 10/2006 | Tsai .................. A61F 7/02 607/96 |
| 2007/0021810 A1 | 1/2007 | Paulin |
| 2007/0118194 A1* | 5/2007 | Mason ............... A61F 7/02 607/104 |
| 2008/0203080 A1* | 8/2008 | Fung ................. A61F 7/034 219/212 |
| 2008/0312722 A1* | 12/2008 | Wang ................ A61F 7/02 607/96 |
| 2010/0312317 A1* | 12/2010 | Baltazar ............ A61F 7/02 607/109 |
| 2012/0259303 A1* | 10/2012 | Carter ............... A61F 13/141 604/385.01 |
| 2014/0371828 A1 | 12/2014 | Whitely |
| 2015/0150716 A1 | 6/2015 | Whitely |
| 2015/0297396 A1 | 10/2015 | Whitely |

OTHER PUBLICATIONS

Hot/Cold Pack—Hot/Cold Pain Relief Information: Bruising, Swelling . . . Downloaded from http://web.archive.org/web/20120801091755/http://www.therapearl.com/ . . . .

TheraPearl Resuable Hot Cold Pack Products: Back Wrap. Downloaded from http://web.archive.org/web/20120802012953/http://www.therapearl.com.

TheraPearl Resuable Hot Cold Pack Products: Shin Wraps. Downloaded from http://web.archive.org/web/20120814063717/http://www.therapearl.com.

TheraPearl Resuable Hot Cold Pack Products: Sport Pack. Downloaded from http://web.archive.org/web/20120814052911/http://www.therapearl.com/ . . . .

TheraPearl Resuable HotCold Pack Products: Contour Downloaded from http://web.archive.org/web/20120802012455/http://www.therapearl.com.

TheraPearl Resuable Hot Cold Pack Products: Neck Wrap. Downloaded from http://web.archive.org/web/20120802224702/http://www.therapearl.com.

Notice of Allowance dated Aug. 17, 2017, by USPTO, re Design U.S. Appl. No. 29/580,183.

* cited by examiner

THERMOTHERAPEUTIC PAD WITH BEADS IN TEXTURED ENVELOPE

FIELD

The present invention relates to thermotherapeutic pads.

BACKGROUND

There are many types of thermotherapeutic pads available. Many use envelopes that are filled with a heat transfer material. The pad can then be heated or cooled to provide the desired thermotherapeutic effect.

Thermotherapeutic pads that use plastic envelopes can suffer from several problems. When the pad is cooled, the envelope may become stiff and unable to easily conform to the body part needing thermal therapy. In addition, condensation may occur at the surface of the envelope, which can cause discomfort. When the pad is heated, the envelope may become excessively hot, which can be potentially unsafe to the user. Although wrapping the pad in a towel has been suggested by some as a possible solution, a person who follows this advice may unknowingly and detrimentally reduce the thermotherapeutic effect by selecting an improper thickness of towel or a towel made of an unsuitable material.

In addition, the heat or cold bearing material inside known thermotherapeutic pads often has a tendency to collect, under influence of gravity or other forces, at locations away from the body part in need of thermal therapy.

Hence, existing thermotherapeutic pads, and particularly those with plastic envelopes, suffer from a number of problems.

SUMMARY

According to one aspect of the present invention, a thermotherapeutic pad includes a sealed envelope comprising a top layer of plastic and a bottom layer of textured plastic. The top layer of plastic and the bottom layer of textured plastic are heat-sealed together. The bottom layer of textured plastic has an outer textured surface and is more thermally insulative than the top layer of plastic. The thermotherapeutic pad further includes a plurality of gel beads contained inside the sealed envelope and liquid contained inside the sealed envelope. The bottom layer can be placed against skin or clothing covering the portion of the body to provide thermal therapy.

According to another aspect of the present invention, a thermotherapeutic pad includes a sealed envelope comprising an at least semitransparent top layer of plastic and an opaque bottom layer of textured plastic. An outer surface of the bottom layer of textured plastic has a warp-knitted fabric made of plastic fiber making the bottom layer of textured plastic more thermally insulative than the top layer of plastic and inhibiting water beading from condensation. The thermotherapeutic pad further includes a plurality of gel beads contained inside the sealed envelope, liquid contained inside the sealed envelope, and air or other gas contained inside the sealed envelope. The bottom layer can be placed against skin or clothing covering the portion of the body to provide thermal therapy.

BRIEF DESCRIPTION OF THE FIGURES

The drawings illustrate, by way of example only, embodiments of the present invention.

DETAILED DESCRIPTION

Figure 1:
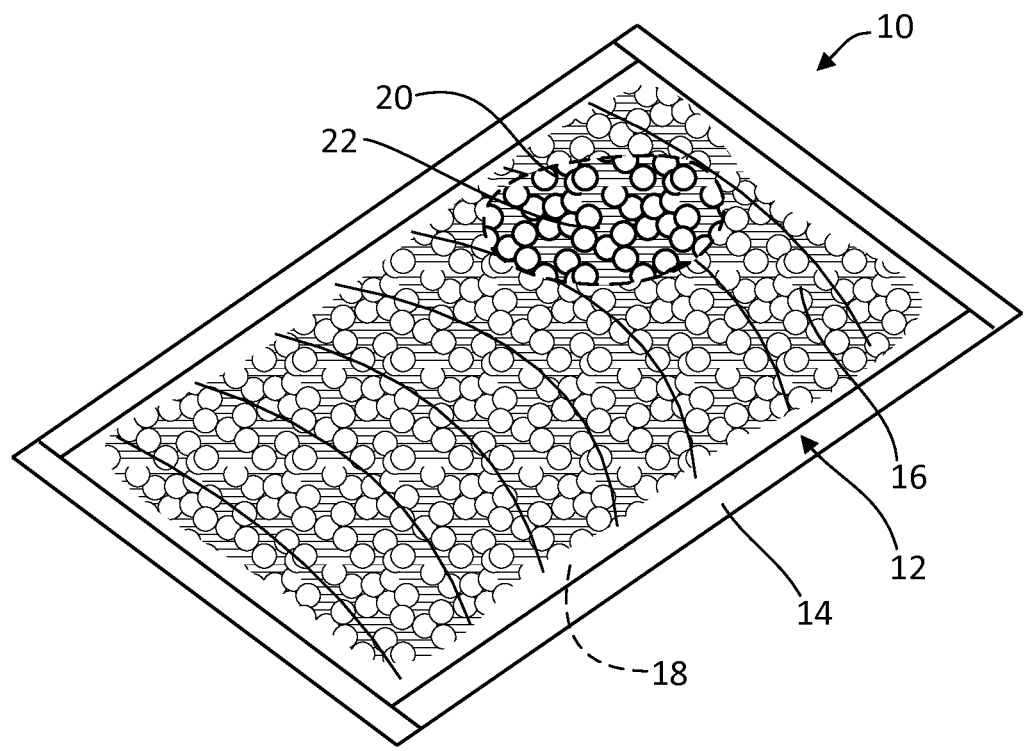
FIG. 1 is a perspective view of a thermotherapeutic pad, as viewed from above.

FIG. 1 shows a thermotherapeutic pad 10 for providing thermal therapy to a portion of a body, such as an arm, leg, neck, shoulder, etc. As will be discussed herein, the thermotherapeutic pad 10 contains gel beads and has a fabric backing to improve the therapeutic heating or cooling effect. The thermotherapeutic pad 10 can be warmed in a microwave oven or cooled in a freezer, so as to provide the desired therapeutic heating or cooling effect. The fabric backing reduces the chance that the pad will hurt or damage the user's skin with too much heat or too much cold, while alleviating the need to wrap the pad in a towel.

The thermotherapeutic pad 10 includes a sealed envelope 12 that may be formed of at least one layer of flexible plastic sheet, which can be heat-sealed at one or more seams 14 that define the outer perimeter of the envelope 12. In this embodiment, the envelope 12 is made of a top layer of plastic 16 and a bottom layer of textured plastic 18, which are overlaid and then heat-sealed together at the seams 14. The terms bottom and top, as used herein, describe opposite directions/ends/surfaces and are not otherwise intended to be limiting. In addition, the envelope 12 is liquid and air impermeable. (The cut-out shown in FIG. 1 is illustrative.)

The layers 16, 18 may include plastic sheet composed of any suitable polymer, such as polyethylene, polyester, polypropylene, nylon, polyvinyl chloride, and combinations of these materials, such as laminates of multiple layers of these materials, as well as laminates of such materials further including natural fibers, fabrics, or paper. In some embodiments, the top layer 16 includes transparent or semitransparent nylon film and the bottom layer 18 includes opaque polyester warp-knitted fabric with a leak resistant backing film that is suitable for heat bonding to the nylon. In some embodiments, one or more of the layers 16, 18 may include cold-crack resistant super-soft vinyl of a thickness of between about 0.10 mm and about 0.20 mm. In some embodiments, one or more of the layers 16, 18 may include super-soft vinyl of a thickness of about 0.15 mm with a cold-crack resistance of about −25 degrees Celsius (about −13 Fahrenheit). The material used may be selected to be free of phthalate and latex.

The thermotherapeutic pad 10 further includes a plurality of gel beads 20 contained inside the sealed envelope 12, as well as liquid 22 contained inside the sealed envelope 12.

In some embodiments, the gel beads 20 are made of glycerol (glycerin) gel, which can include glycerol and a suitable binder, such as sorbitol. Other gel materials may also be used. The gel beads 20 can be resiliently deformable and can be dyed one or more colors. The material and size of the gel beads can be selected to provide a suitable heat capacity and heat transfer rate.

In various embodiments, the liquid 22 comprises water, glycerol, or a mixture thereof. The composition of the liquid 22 can be selected to provide a suitable heat capacity and heat transfer rate.

The amount of gel beads 20 and liquid 22 and the relative proportion of gel beads 20 to liquid 22 can be selected to provide a target thermotherapeutic effect, as well as to allow the envelope to readily conform to the body part undergoing therapy. In some embodiments, a minimal amount of liquid is used, enough to substantially wet the gel beads, such that heat is transferred between the gel beads by the liquid, but excess liquid does not pool or collect.

The envelope 12 can further contain an amount of air or other gas. This can prevent unwanted heat transfer between the pad 10 and a hand, when the pad 10 is held from above. That is, the gel beads 20 and liquid 22 tend to collect at lower areas of the pad 10 due to gravity, while air or other gas remains in upper areas of the pad 10, which may be gripped by the user. Since air has a lower heat capacity and heat transfer rate than the gel beads 20 and liquid 22, gripping air-containing regions of the pad 10 can increase user comfort.

In some embodiments, the top layer of plastic 16 is at least semitransparent, thereby allowing the beads 20 and liquid 22 contained within the thermotherapeutic pad 10 to be visible to the user. This can advantageously allow the user to determine which area of the pad 10 to grip.

Figure 2:
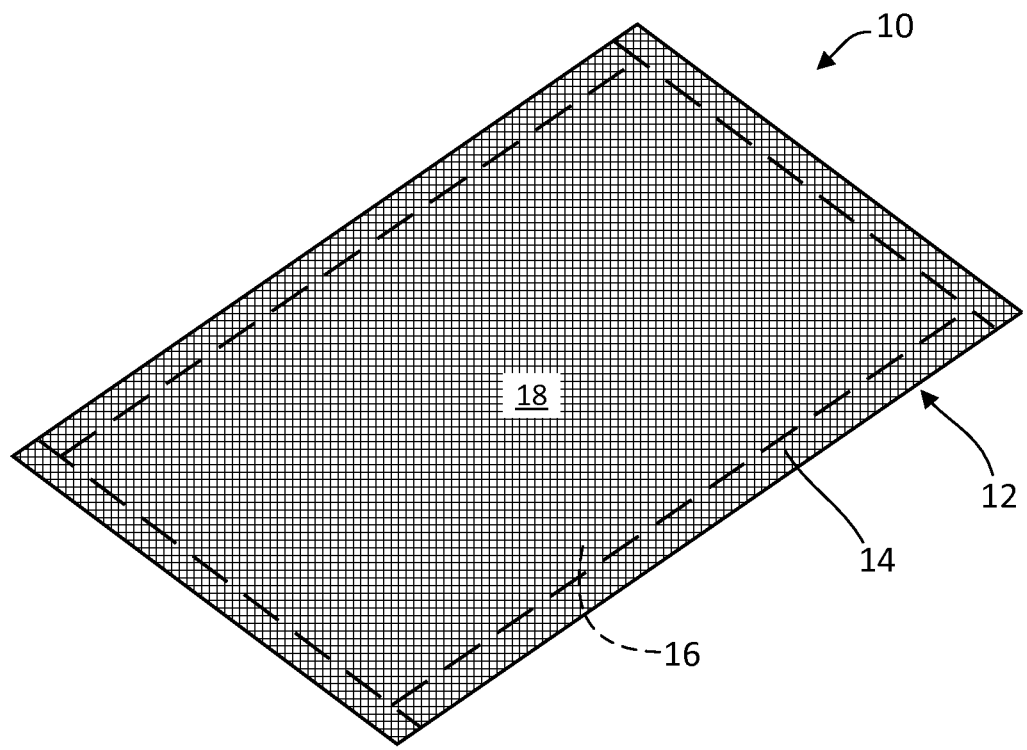
FIG. 2 is a perspective view of the thermotherapeutic pad, as viewed from below.

FIG. 2 shows the bottom layer of textured plastic 18, which has an outer textured surface that is more thermally insulative than the top layer of plastic 16. When the thermotherapeutic pad 10 is in use, the bottom layer 18 can be placed against the skin or clothing covering the portion of the body to provide the thermal therapy.

In some embodiments, the outer textured surface of the bottom layer 18 has a fiber texture for placement in direct contact with the skin. The fiber texture provides an amount of thermal insulation to slow or disperse the cooling or heating effect of the thermotherapeutic pad 10 and prevent the skin for becoming too cold or too hot. Further, the fiber texture may reduce water beading from condensation, thereby increasing comfort when using the pad 10. The fiber texture can eliminate the need to use a wrap or towel around the thermotherapeutic pad 10, and therefore reduce the time it takes to prepare and apply the thermotherapeutic pad 10. The thermotherapeutic pad 10 can be used against clothes as well, and the fiber texture does not limit potential modes of application of the thermotherapeutic pad 10.

The fiber texture can be formed separate from the plastic sheet, and can include a fabric knit, a fabric weave, paper, or similar material that is then joined to the plastic sheet, by adhesive, heat-sealing, or other technique. Alternatively, the fiber texture can be formed by filaments or fibers that are integral to the plastic sheet and made of the same material as the plastic sheet. In some embodiments, the fiber texture is provided by a warp-knitted fabric made of plastic fiber, such as warp-knitted 100% polyester fabric at about 150 (+/−5) grams/square meter.

Figure 3:
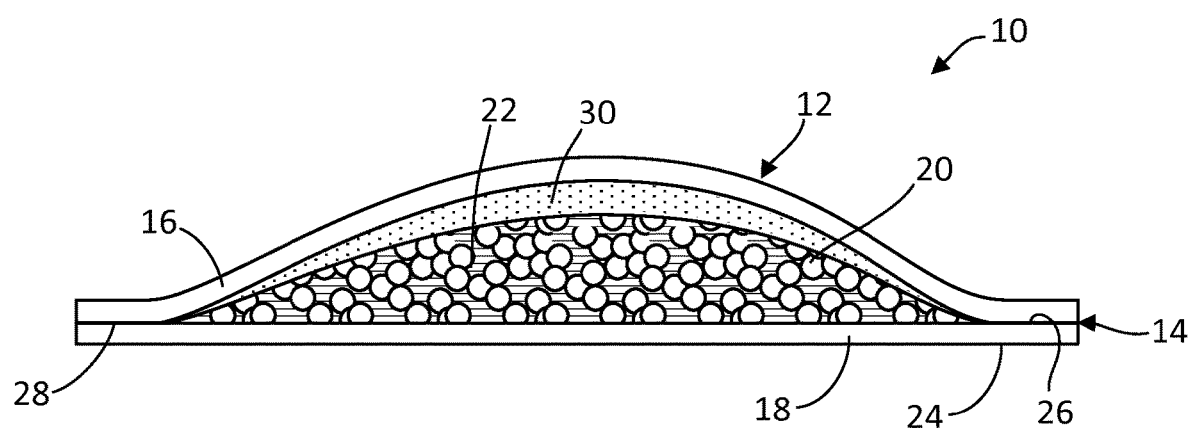
FIG. 3 is a cross-sectional view of the thermotherapeutic pad.

As shown in FIG. 3, the bottom layer 18 of textured plastic 18 has the fiber texture on the outside surface 24 and bare plastic on the inside surface 26. The fiber texture provides the bottom layer 18 with increased thermal insulation as discussed above. The bare plastic allows the bottom layer 18 to be liquid and gas impermeable. The bare plastic on the inside surface 26 of the bottom layer 18 further allows the bottom layer 18 to be joined to another bare plastic surface 28 of the top layer 16 by heat-sealing at seams 14.

As further shown in FIG. 3, in some situations, the gel beads 20 and liquid 22 contained in the thermotherapeutic pad 10 will settle under influence of gravity, causing air 30 or other gas contained within the thermotherapeutic pad 10 to gather in one or more areas at which the pad 10 can be gripped without unwanted heating or cooling of the gripping hand.

In use, the thermotherapeutic pad 10 is heated in a microwave oven (or similar device) or cooled in freezer (or similar device) for a suitable time. The user then applies the insulative bottom layer 18 to the body part in need of thermal therapy. The user can look through the semitransparent top layer 16 to find an area in the pad that does not presently contain beads 20 or liquid 22, and grip the pad there. If the thermal therapeutic effect is insufficient, or after the effect declines during use, the user can flip the pad 10 over, so that the less thermally insulative top layer 16 contacts the body part to continue the therapy.

Figure 4:
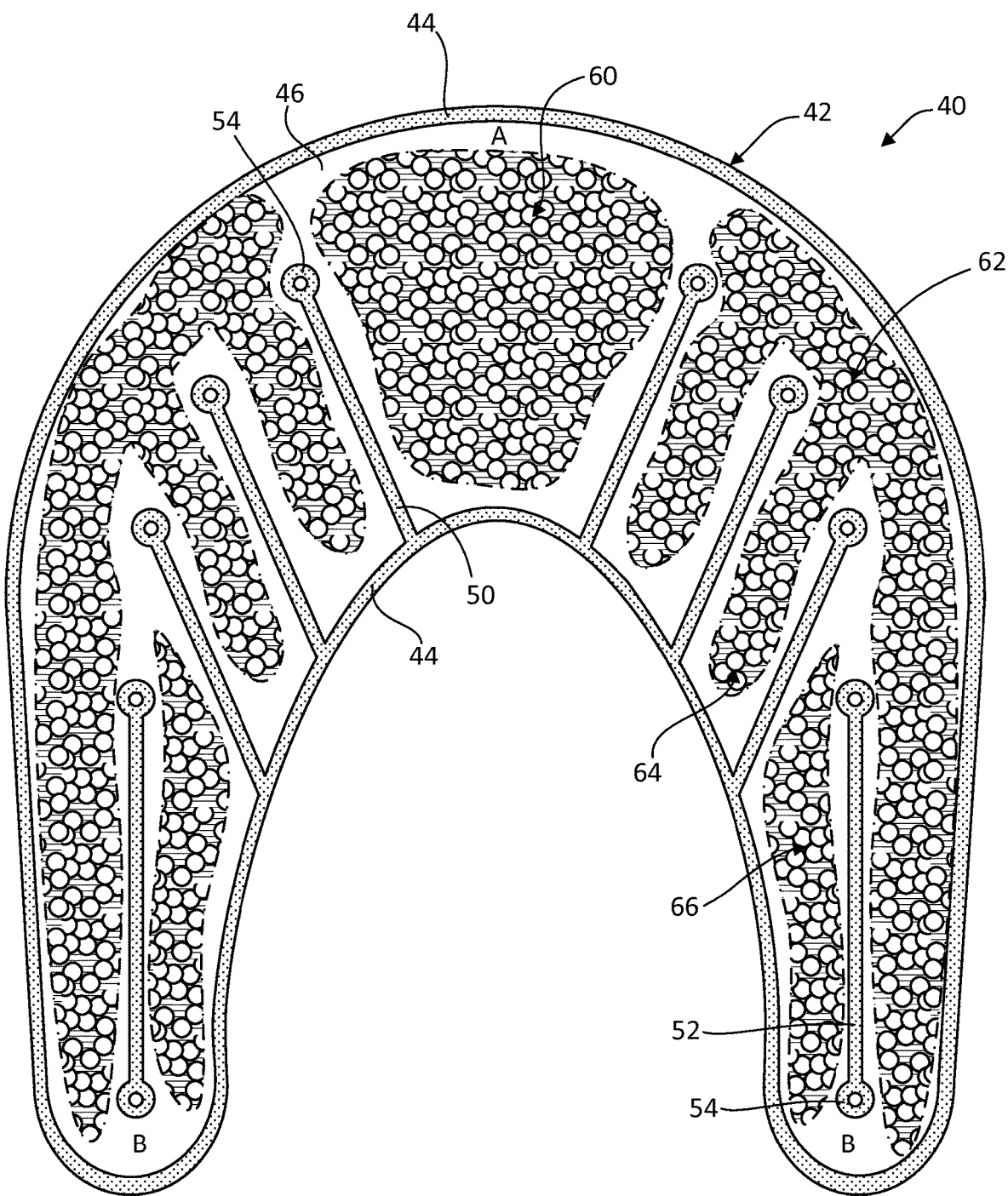
FIG. 4 is a front view of another thermotherapeutic pad, which has a U-shaped envelope and baffles.

FIG. 4 shows another thermotherapeutic pad 40 as viewed from the front. The thermotherapeutic pad 40 is similar to the thermotherapeutic pad 10, and only differences will be discussed in detail. Features and aspects of the other thermotherapeutic pads described herein can be used for the thermotherapeutic pad 40.

The thermotherapeutic pad 40 is U-shaped so as to fit over a person's shoulders to apply thermal therapy to the person's shoulders, neck, and upper back.

The thermotherapeutic pad 40 includes a sealed envelope 42 that may be formed of at least one layer of flexible plastic sheet, which can be heat-sealed at one or more outer seams 44 that define the outer perimeter of the envelope 42. In this embodiment, the envelope 42 is made of a top layer 46 of plastic and a bottom layer 48 of textured plastic (shown in FIG. 5). The top layer 46 may be transparent or semitransparent and the bottom layer 48 may be opaque.

A mixture of gel beads and liquid contained inside the sealed envelope 42. The mixture may be visible through the top layer 46, when the top layer 46 is selected to be transparent or semitransparent.

The thermotherapeutic pad 40 further includes internal baffles defined by baffle seams 50, 52. A plurality of edge-connected baffle seams 50 intersect with the outer seam 44 and extend from the outer seam 44 to endpoints 54 internal to the envelope 42. A plurality of internal baffle seams 52 are completely internal to the envelope 42 and do not intersect with the outer seam 44. Each internal baffle seam 52 terminates at two endpoints 54. The endpoints 54 can be circular in shape and larger than the width of the baffle seams 50, 52. Enlarged endpoints 54 serve as reinforcements to prevent the baffle seams 50, 52 from peeling apart, a problem that would tend to begin at the ends of the seams 50, 52.

The baffle seams 50, 52 and their endpoints 54 can be formed by local joining of the top and bottom layers 46, 48 of the envelope 42 using, for example, the same heat-sealing process that forms the outer seam 44. For example, the top and bottom layers 46, 48 can be inserted into a single heat-sealing press that has sealing pattern defining the outer seam 44 and the baffle seams 50, 52 with their endpoints 54. A small opening may be left in the outer seam 44 to allow for filling of the envelope 42 with gel beads and liquid, and such an opening may be heat-sealed after filling.

The baffle seams 50, 52 can be arranged to cause the gel beads inside the envelope 42 to tend to collect in pockets, while still allowing movement of the gel beads and liquid throughout the entire envelope 42. The spacing and sizes of the baffle seams 50, 52 can be selected to promote even distribution of the gel beads and prevent a large amount of gel beads from collecting in the same region. Hence, the baffle seams 50, 52 can increase the thermotherapeutic effectiveness of the pad 40 by reducing the chance that one region of the pad will be without gel beads while another region of the pad has too many gel beads.

In the example shown, several pockets of gel beads are shown for explanatory purposes. A first pocket 60 is defined to contain gel beads in a region of the pad 40 that contacts the back of the neck and upper back of the person using the pad. Each of two second pockets 62 includes a larger region, as well as several lobes 64 to evenly distribute gel beads along the shoulder regions of the pad 40. Each of two third pockets 66 helps position gel beads at the inner shoulder region of the pad 40.

Even distributions of gel beads are not limited to precisely even distributions, and suitable even distributions can vary considerably.

As can be seen, without the baffle seams 50, 52, gel beads would tend to congregate towards locations A and B under influence of gravity when the pad 40 straddles the shoulders. This would reduce the heat or cooling available to the neck and upper shoulder regions, which are typically prime targets for thermal therapy. Hence, the baffle seams 50, 52 increase the effectiveness and convenience of the pad 40 and allow heat or cooling to be targeted to important regions of the body.

Figure 5:
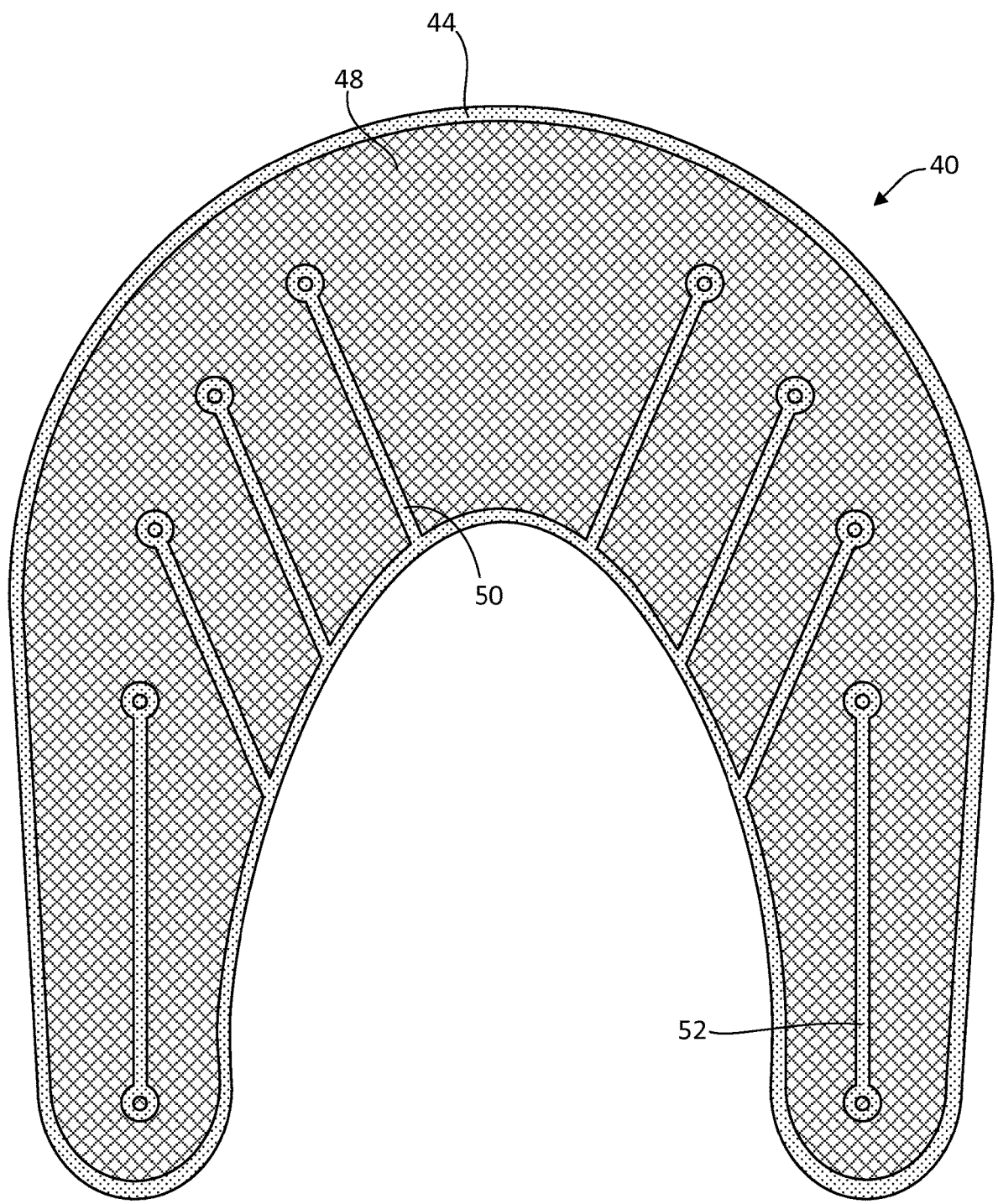
FIG. 5 is a rear view of the U-shaped thermotherapeutic pad.

FIG. 5 shows the thermotherapeutic pad 40 as viewed from the back. The bottom layer 48 of textured plastic can include a fiber texture, as discussed elsewhere herein. When the bottom layer 48 is placed against the body, the fiber texture acts as an insulator that can help reduce the chance that the pad 40 will hurt or damage the user's skin with too much heat or too much cold, while alleviating the need to wrap the pad 40 in a towel. Further, the user or caregiver may view the gel beads through the transparent/semitransparent top layer 46 to confirm that heating/cooling is being delivered to the necessary regions of the body.

Figure 6:
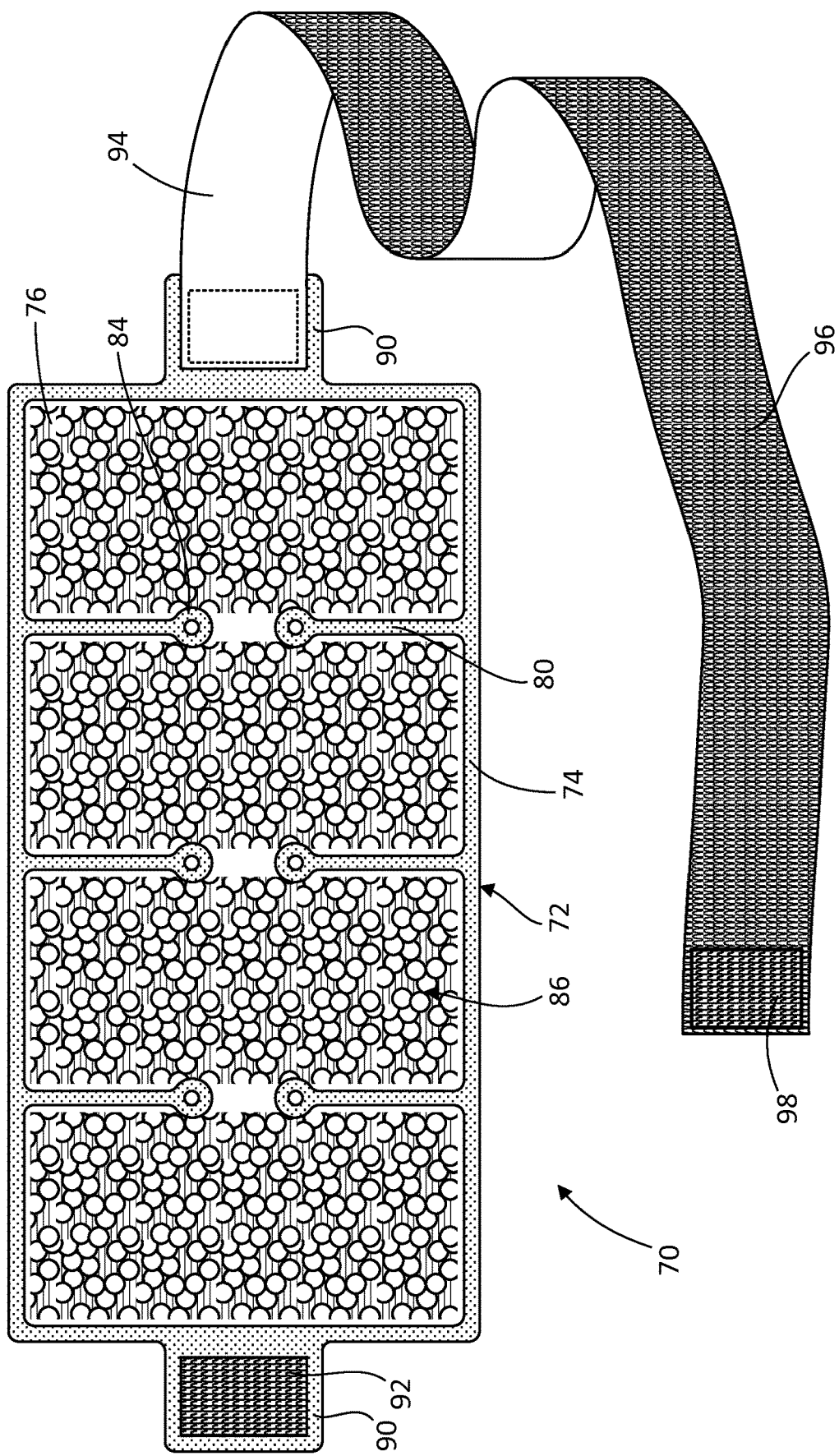
FIG. 6 is a front view of another thermotherapeutic pad, which has baffles and a strap.

FIG. 6 shows another thermotherapeutic pad 70 as viewed from the front. The thermotherapeutic pad 70 is similar to the thermotherapeutic pad 10, and only differences will be discussed in detail. Features and aspects of the other thermotherapeutic pads described herein can be used for the thermotherapeutic pad 70.

The thermotherapeutic pad 70 is rectangular so as to fit a person's abdomen, leg, arm, or other body part.

The thermotherapeutic pad 70 includes a sealed envelope 72 that may be formed of at least one layer of flexible plastic sheet, which can be heat-sealed at one or more outer seams 74 that define the outer perimeter of the envelope 72. In this embodiment, the envelope 72 is made of a top layer 76 of plastic and a bottom layer 78 of textured plastic (shown in FIG. 7). The top layer 76 may be transparent or semitransparent and the bottom layer 78 may be opaque.

A mixture of gel beads and liquid contained inside the sealed envelope 72, with the mixture visible through the top layer 76 if selected to be transparent or semitransparent.

The thermotherapeutic pad 70 further includes internal baffles defined by edge-connected baffle seams 80 that intersect with the outer seam 74 and extend from the outer seam 74 to endpoints 84 internal to the envelope 72. The endpoints 84 can be circular in shape and larger than the width of the baffle seams 80 to provide reinforcement to prevent the baffle seams 80 from peeling apart.

As discussed elsewhere herein, the baffle seams 80 and their endpoints 84 can be formed by local joining of the top and bottom layers 76, 78 of the envelope 72 using, for example, a heat-sealing process.

The baffle seams 80 can be arranged to cause the gel beads inside the envelope 72 to tend to collect in pockets, while still allowing movement of the gel beads and liquid throughout the entire envelope 72. The spacing and sizes of the baffle seams 80 can be selected to promote even distribution of the gel beads and prevent a large amount of gel beads from congregating in the same region. Hence, the baffle seams 80 can increase the thermotherapeutic effectiveness of the pad 70 by reducing localized concentrations of gel beads.

In the example shown, a series of similar rectangular pockets 86 of gel beads are defined by the baffle seams 80. The baffle seams 80 do not completely isolate adjacent pockets 86, so gel beads and liquid can move among the pockets 86. However, movement of gel beads is restricted somewhat by the baffle seams 80, so as to prevent unsuitable congregations of gel beads or voids. Hence, the baffle seams 80 increase the effectiveness and convenience of the pad 70.

The thermotherapeutic pad 70 can further include end flaps 90, which in this embodiment are situated at the short ends of the rectangular envelope 72. For strength and leak prevention, the end flaps 90 can be formed by material of top and bottom layers 76, 78 heat sealed together. The end flaps 90 may be formed in the same manner as the outer seam 74 and the baffles seams 80.

Attached to one end flap 90 is a first fastener 92, which may include one side of a hook-and-loop fastener. In this example, the first fastener 92 is a hook side. Attached to the other end flap 90 is a strap 94, which may be stitched to the flap 90 or attached by other means. The strap 94 can be made of flexible and comfortable fabric material and may include a region of loop elements 96 of a hook-and-loop fastener. The region of loop elements 96 may extend a portion of the length of the strap 94 or may extend the entire length of the strap 94. The region of loop elements 96 may face opposite the first fastener 92. A second fastener 98 can be attached at the free end of the strap 94 and may face, for example, the same direction as the region of loop elements 96. The second fastener 98 can be a hook side of a hook-and-loop fastener. With this arrangement of fasteners, the thermotherapeutic pad 70 and strap 94 can be wrapped around a person's body part in a number of different ways. It should be mentioned that hook-and-loop fasteners are merely examples, and other types of fasteners can be used, such as buttons, clips, buckles, and the like. Further, the fiber texture used for the envelope 72 can be selected to be engageable with any hook side fasteners used.

Figure 7:
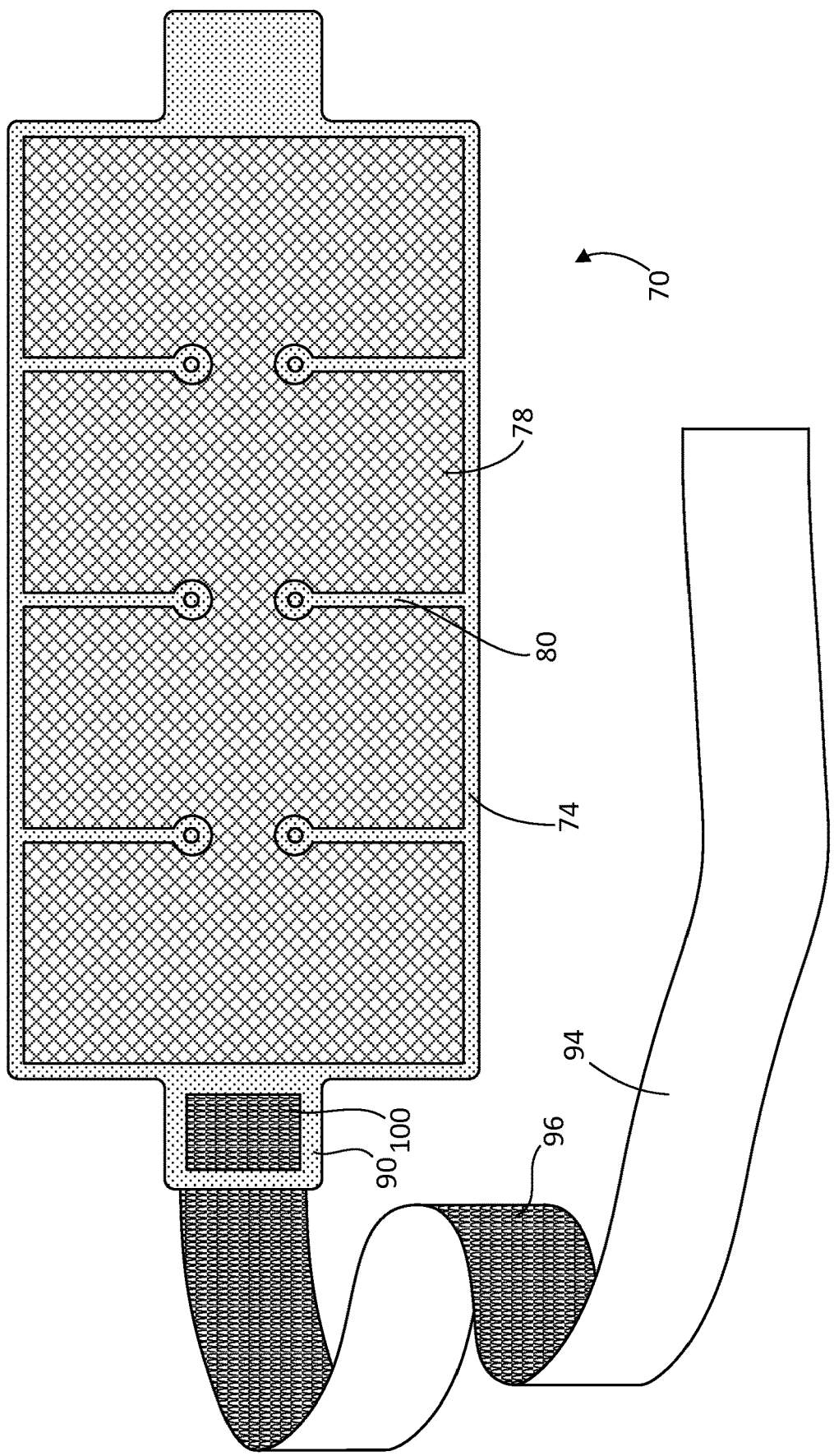
FIG. 7 is a rear view of the thermotherapeutic pad with strap.

FIG. 7 shows the thermotherapeutic pad 70 as viewed from the back. The bottom layer 78 of textured plastic can include a fiber texture, as discussed elsewhere herein. When the bottom layer 78 is placed against the body, the fiber texture acts as an insulator that can help reduce the chance that the pad 70 will hurt or damage the user's skin with too much heat or too much cold, while alleviating the need to wrap the pad 70 in a towel. Further, the user or caregiver may view the gel beads through the transparent/semitransparent top layer 76 to confirm that heating/cooling is being delivered to the necessary regions of the body.

The thermotherapeutic pad 70 may further include a third fastener 100 attached to the bottom layer 78 on the same flap 90 to which the strap 94 is attached. The third fastener 100 may face the same direction as the region of loop elements 96 on the strap 94. In this example, the third fastener 100 is a loop side of a hook-and-loop fastener, which can facilitate other modes of wrapping and securing the thermotherapeutic pad 70 to the body in conjunction with the first and second, hook-side fasteners 92, 98 (FIG. 6).

As can be seen from the above, the present invention provides a thermotherapeutic pad that is convenient and safe to use in various therapeutic situations, and that is readily manufacturable.

While the foregoing provides certain non-limiting example embodiments, it should be understood that combinations, subsets, and variations of the foregoing are contemplated. The monopoly sought is defined by the claims.

What is claimed is:

1. A thermotherapeutic pad for providing thermal therapy to a portion of a body, the thermotherapeutic pad comprising:
   a sealed envelope comprising a top layer of plastic and a bottom layer of textured plastic, the top layer of plastic and the bottom layer of textured plastic being heat-sealed together, the bottom layer of textured plastic having an outer textured surface, wherein the outer textured surface has a fiber texture that causes the bottom layer of textured plastic to be more thermally insulative than the top layer of plastic, the fiber texture being formed by filaments or fibers that are integral to the bottom layer and made of a same material as the bottom layer;
   a plurality of gel beads contained inside the sealed envelope;
   a baffle positioned to evenly distribute the gel beads inside the sealed envelope, the baffle defined by a baffle seam and an endpoint, the endpoint being wider than the baffle seam to provide reinforcement; and
   liquid contained inside the sealed envelope,
   wherein the bottom layer is for placement in direct contact with skin of a user to prevent thermal shock to the user, the bottom layer of textured plastic comprises an inside surface of liquid- and gas-impermeable plastic contacting the liquid contained inside the sealed envelope, and the bottom layer of textured plastic comprises a layer of nylon, a layer of polyethylene, and a layer of polyester, wherein the layer of polyester comprises the outer textured surface and the layer of polyethylene comprises the inside surface.

2. The thermotherapeutic pad of claim 1, wherein the layer of polyester of the bottom layer of textured plastic is configured to inhibit water beading from condensation.

3. The thermotherapeutic pad of claim 1, wherein the layer of polyester of the bottom layer of textured plastic is warp-knitted fabric of plastic fiber.

4. The thermotherapeutic pad of claim 1, wherein the bottom layer of textured plastic is opaque.

5. The thermotherapeutic pad of claim 1, wherein the top layer of plastic is at least semitransparent.

6. The thermotherapeutic pad of claim 1, wherein the gel beads are made of glycerol gel.

7. The thermotherapeutic pad of claim 1, wherein the liquid comprises water.

8. The thermotherapeutic pad of claim 1, wherein the liquid comprises glycerol.

9. The thermotherapeutic pad of claim 1, further comprising air or other gas contained within the sealed envelope.

10. The thermotherapeutic pad of claim 1, wherein the baffle seam is formed from the top layer of plastic and the bottom layer of textured plastic.

11. The thermotherapeutic pad of claim 10, wherein the baffle seam intersects with an outer seam that seals the envelope.

12. The thermotherapeutic pad of claim 10, wherein the baffle seam does not intersect with an outer seam that seals the envelope.

13. A thermotherapeutic pad for providing thermal therapy to a portion of a body, the thermotherapeutic pad comprising:
    a sealed envelope comprising an at least semitransparent top layer of plastic and an opaque bottom layer of textured plastic, an outer surface of the bottom layer of textured plastic having a warp-knitted fabric made of plastic fiber making the bottom layer of textured plastic more thermally insulative than the top layer of plastic and inhibiting water beading from condensation, wherein the warp-knitted fabric made of plastic fiber is integral to the bottom layer and is made of a same material as the bottom layer;
    a plurality of gel beads contained inside the sealed envelope;
    a baffle positioned to evenly distribute the gel beads inside the sealed envelope, the baffle defined by a baffle seam and an endpoint, the endpoint being wider than the baffle seam to provide reinforcement;
    liquid contained inside the sealed envelope; and
    air or other gas contained inside the sealed envelope,
    wherein the bottom layer is for placement in direct contact with skin of a user to prevent thermal shock to the user, the bottom layer of textured plastic comprises an inside surface of liquid- and gas-impermeable plastic contacting the liquid contained inside the sealed envelope, and the bottom layer of textured plastic comprises a layer of nylon, a layer of polyethylene, and a layer of polyester, wherein the layer of polyester comprises the outer textured surface and the layer of polyethylene comprises the inside surface.

14. The thermotherapeutic pad of claim 13, wherein the plurality of gel beads is made of glycerol gel and the liquid comprises water, glycerol, or a mixture of such.

15. The thermotherapeutic pad of claim 13, wherein the baffle seam is formed from the top layer of plastic and the bottom layer of textured plastic.

16. The thermotherapeutic pad of claim 15, wherein the baffle seam intersects with an outer seam that seals the envelope.

17. The thermotherapeutic pad of claim 15, wherein the baffle seam does not intersect with an outer seam that seals the envelope.

18. A thermotherapeutic pad for providing thermal therapy to a portion of a body, the thermotherapeutic pad comprising:
    a sealed envelope comprising an at least semitransparent top layer of plastic and an opaque bottom layer of textured plastic, the top layer of plastic and the bottom layer of textured plastic being heat-sealed together, the bottom layer of textured plastic having an outer textured surface, wherein the outer textured surface has a fiber texture that causes the bottom layer of textured plastic to be more thermally insulative than the top layer of plastic, the fiber texture being formed by filaments or fibers that are integral to the bottom layer and made of a same material as the bottom layer;
    a plurality of gel beads contained inside the sealed envelope; and
    liquid contained inside the sealed envelope,
    wherein the bottom layer is for placement in direct contact with skin of a user to prevent thermal shock to the user, the bottom layer of textured plastic comprises an inside surface of liquid- and gas-impermeable plastic contacting the liquid contained inside the sealed envelope, and the bottom layer of textured plastic comprises a layer of nylon, a layer of polyethylene, and a layer of polyester, wherein the layer of polyester comprises the outer textured surface and the layer of polyethylene comprises the inside surface.

19. The thermotherapeutic pad of claim 18, wherein the layer of polyester of the bottom layer of textured plastic is configured to inhibit water beading from condensation.

20. The thermotherapeutic pad of claim 18, wherein the layer of polyester of the bottom layer of textured plastic is warp-knitted fabric of plastic fiber.

21. The thermotherapeutic pad of claim 18, wherein the sealed envelope is liquid and air impermeable.

22. A thermotherapeutic pad for providing thermal therapy to a portion of a body, the thermotherapeutic pad comprising:
   a sealed envelope comprising an at least semitransparent top layer of plastic and an opaque bottom layer of textured plastic, an outer surface of the bottom layer of textured plastic having a warp-knitted fabric made of plastic fiber making the bottom layer of textured plastic more thermally insulative than the top layer of plastic and inhibiting water beading from condensation, wherein the warp-knitted fabric made of plastic fiber is integral to the bottom layer and is made of a same material as the bottom layer;
   a plurality of gel beads contained inside the sealed envelope;
   liquid contained inside the sealed envelope; and
   air or other gas contained inside the sealed envelope,
   wherein the bottom layer is for placement in direct contact with skin of a user to prevent thermal shock to the user, wherein the bottom layer of textured plastic comprises an inside surface of liquid- and gas-impermeable plastic contacting the liquid contained inside the sealed envelope, and the bottom layer of textured plastic comprises a layer of nylon, a layer of polyethylene, and a layer of polyester, wherein the layer of polyester comprises the outer textured surface and the layer of polyethylene comprises the inside surface.

23. The thermotherapeutic pad of claim 22, wherein the sealed envelope is liquid and air impermeable.

24. A thermotherapeutic pad for providing thermal therapy to a portion of a body, the thermotherapeutic pad comprising:
   a sealed envelope comprising a top layer of plastic and a bottom layer of textured plastic, the top layer of plastic and the bottom layer of textured plastic being heat-sealed together, the bottom layer of textured plastic having an outer textured surface, wherein the outer textured surface has a fiber texture that causes the bottom layer of textured plastic to be more thermally insulative than the top layer of plastic, the fiber texture being formed by filaments or fibers that are integral to the bottom-layer and made of a same material as the bottom layer,
   a plurality of gel beads contained inside the sealed envelope,
   a baffle positioned to evenly distribute the gel beads inside the sealed envelope, the baffle defined by a baffle seam and an endpoint, the endpoint being wider than the baffle seam to provide reinforcement; and
   liquid contained inside the sealed envelope,
   wherein the bottom layer is for placement in direct contact with skin of a user to prevent thermal shock to the user, the top layer of plastic comprises an inside surface of liquid- and gas-impermeable plastic contacting the liquid contained inside the sealed envelope, and the top layer of plastic comprises a layer of nylon and a layer of polyethylene, wherein the layer of polyethylene comprises the inside surface of the top layer of plastic.

25. A thermotherapeutic pad for providing thermal therapy to a portion of a body, the thermotherapeutic pad comprising:
   a sealed envelope comprising an at least semitransparent top layer of plastic and an opaque bottom layer of textured plastic, an outer surface of the bottom layer of textured plastic having a warp-knitted fabric made of plastic fiber making the bottom layer of textured plastic more thermally insulative than the top layer of plastic and inhibiting water beading from condensation, wherein the warp-knitted fabric made of plastic fiber is integral to the bottom layer and is made of a same material as the bottom layer;
   a plurality of gel beads contained inside the sealed envelope;
   a baffle positioned to evenly distribute the gel beads inside the sealed envelope, the baffle defined by a baffle seam and an endpoint, the endpoint being wider than the baffle seam to provide reinforcement;
   liquid contained inside the sealed envelope, and
   air or other gas contained inside the sealed envelope,
   wherein the bottom layer is for placement in direct contact with skin of a user to prevent thermal shock to the user, the top layer of plastic comprises an inside surface of liquid- and gas-impermeable plastic contacting the liquid contained inside the sealed envelope, and the top layer of plastic comprises a layer of nylon and a layer of polyethylene, wherein the layer of polyethylene comprises the inside surface of the top layer of plastic.

26. A thermotherapeutic pad for providing thermal therapy to a portion of a body, the thermotherapeutic pad comprising:
   a sealed envelope comprising an at least semitransparent top layer of plastic and an opaque bottom layer of textured plastic, the top layer of plastic and the bottom layer of textured plastic being heat-sealed together, the bottom layer of textured plastic having an outer textured surface, wherein the outer textured surface has a fiber texture that causes the bottom layer of textured plastic to be more thermally insulative than the top layer of plastic, the fiber texture being formed by filaments or fibers that are integral to the bottom layer and made of a same material as the bottom layer;
   a plurality of gel beads contained inside the sealed envelope; and
   liquid contained inside the sealed envelope,
   wherein the bottom layer is for placement in direct contact with skin of a user to prevent thermal shock to the user, the top layer of plastic comprises an inside surface of liquid- and gas-impermeable plastic contacting the liquid contained inside the sealed envelope and the top layer of plastic comprises a layer of nylon and a layer of polyethylene, wherein the layer of polyethylene comprises the inside surface of the top layer of plastic.

27. A thermotherapeutic pad for providing thermal therapy to a portion of a body, the thermotherapeutic pad comprising:
   a sealed envelope comprising an at least semitransparent top layer of plastic and an opaque bottom layer of textured plastic, an outer surface of the bottom layer of textured plastic having a warp-knitted fabric made of plastic fiber making the bottom layer of textured plastic more thermally insulative than the top layer of plastic and inhibiting water beading from condensation, wherein the warp-knitted fabric made of plastic fiber is integral to the bottom layer and is made of a same material as the bottom layer;

a plurality of gel beads contained inside the sealed envelope;

liquid contained inside the sealed envelope; and air or other gas contained inside the sealed envelope, wherein the bottom layer is for placement in direct contact with skin of a user to prevent thermal shock to the user, the top layer of plastic comprises an inside surface of liquid- and gas-impermeable plastic contacting the liquid contained inside the sealed envelope, and the top layer of plastic comprises a layer of nylon and a layer of polyethylene, wherein the layer of polyethylene comprises the inside surface of the top layer of plastic.

* * * * *

US010632011C1

(12) EX PARTE REEXAMINATION CERTIFICATE (12603rd)
United States Patent
Whitely

(10) Number: US 10,632,011 C1
(45) Certificate Issued: May 17, 2024

(54) THERMOTHERAPEUTIC PAD WITH BEADS IN TEXTURED ENVELOPE

(71) Applicant: Rapid Aid Corp., Mississauga (CA)

(72) Inventor: Jeffrey Thomas Whitely, Millgrove (CA)

(73) Assignee: RAPID AID CORP., Mississauga (CA)

Reexamination Request:
No. 90/014,685, Feb. 26, 2021

Reexamination Certificate for:
Patent No.: 10,632,011
Issued: Apr. 28, 2020
Appl. No.: 14/136,639
Filed: Dec. 20, 2013

(51) Int. Cl.
*A61F 7/02* (2006.01)
*A61F 7/10* (2006.01)

(52) U.S. Cl.
CPC ........ *A61F 7/02* (2013.01); *A61F 2007/0209* (2013.01); *A61F 2007/0219* (2013.01); *A61F 2007/0228* (2013.01)

(58) Field of Classification Search
None
See application file for complete search history.

(56) References Cited

To view the complete listing of prior art documents cited during the proceeding for Reexamination Control Number 90/014,685, please refer to the USPTO's Patent Electronic System.

*Primary Examiner* — Glenn K Dawson

(57) ABSTRACT

A thermotherapeutic pad includes a sealed envelope having a top layer of plastic and a bottom layer of textured plastic. The top layer of plastic and the bottom layer of textured plastic can be heat-sealed together. The bottom layer of textured plastic has an outer textured surface and is more thermally insulative than the top layer of plastic. A plurality of gel beads and liquid are contained inside the sealed envelope. The bottom layer of the pad can be placed against the skin or clothing to provide thermal therapy. Baffles can be provided inside the sealed envelope to promote even distribution of gel beads.

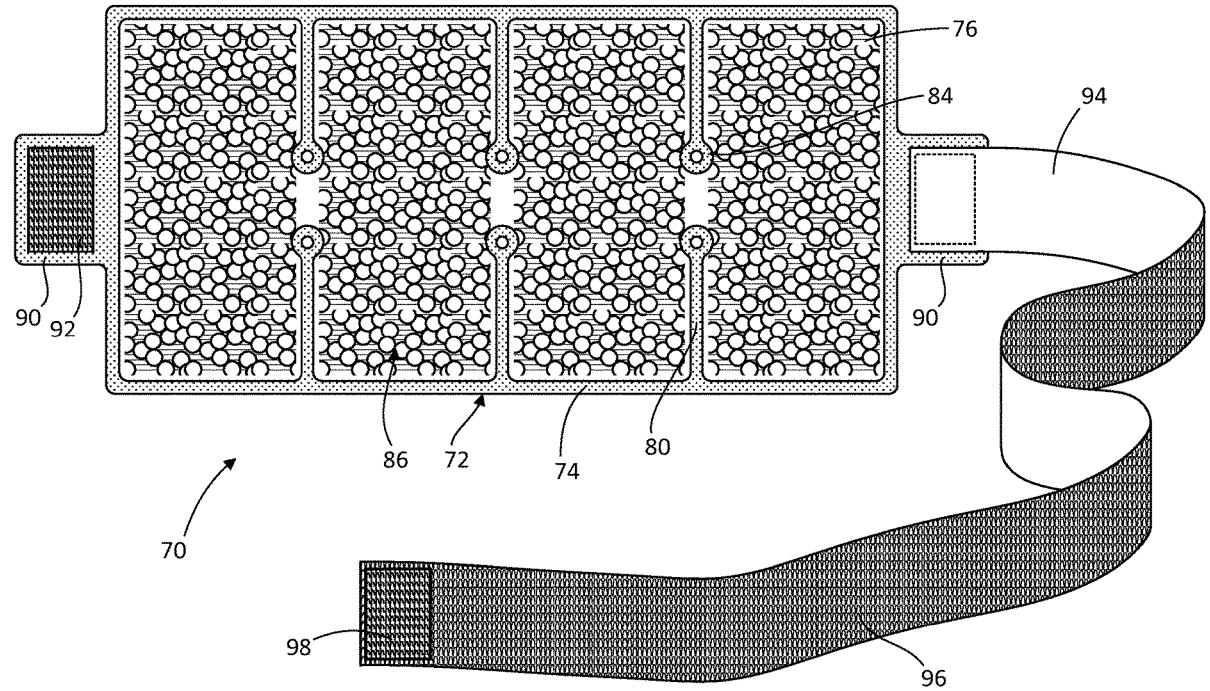

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-27 are cancelled.

* * * * *